(12) United States Patent
Hight et al.

(10) Patent No.: US 11,833,087 B2
(45) Date of Patent: Dec. 5, 2023

(54) SUBJECT AND SURGICAL EQUIPMENT MONITORING SYSTEMS

(71) Applicant: Allen Medical Systems, Inc., Batesville, IN (US)

(72) Inventors: Joshua C. Hight, Somerville, MA (US); Varad Narayan Srivastava, Loveland, OH (US)

(73) Assignee: Allen Medical Systems, Inc., Batesville, IN (US)

( * ) Notice: Subject to any disclaimer, the term of this patent is extended or adjusted under 35 U.S.C. 154(b) by 0 days.

(21) Appl. No.: 17/747,610

(22) Filed: May 18, 2022

(65) Prior Publication Data

US 2022/0273513 A1    Sep. 1, 2022

Related U.S. Application Data

(62) Division of application No. 15/343,577, filed on Nov. 4, 2016, now Pat. No. 11,364,168.
(Continued)

(51) Int. Cl.
*A61G 13/12* (2006.01)
*A61B 5/00* (2006.01)
(Continued)

(52) U.S. Cl.
CPC ........ *A61G 13/1215* (2013.01); *A61B 5/0077* (2013.01); *A61B 5/1128* (2013.01);
(Continued)

(58) Field of Classification Search
CPC .. A61G 13/121; A61G 13/1215; A61G 13/00; A61G 13/0036; A61G 13/0054;
(Continued)

(56) References Cited

U.S. PATENT DOCUMENTS

| 4,752,064 A | 6/1988 | Voss |
| 4,819,257 A | 4/1989 | Grasser et al. |

(Continued)

FOREIGN PATENT DOCUMENTS

| DE | 102014104529 A1 | 10/2015 |
| EP | 1028684 B1 | 3/2004 |

(Continued)

OTHER PUBLICATIONS

Mittal et al, Real Time Vision System for Collision Detection, Indian Institute of Technology, Delhi, New Delhi 110016.
(Continued)

*Primary Examiner* — Michelle J Lee
(74) *Attorney, Agent, or Firm* — Dinsmore & Shohl LLP

(57) ABSTRACT

A surgical monitoring system including a machine vision sensor, an electronic controller communicatively coupled to the machine vision sensor, the electronic controller including a processor and a memory storing a computer readable instruction set, where, when the computer readable instruction set is executed by the processor, the electronic controller, detects a position of a subject with the machine vision sensor, detects a position of a person support apparatus, compares the detected position of the subject with the detected position of the person support apparatus, and determines if the detected position of the subject and the detected position of the person support apparatus indicates that the subject is not aligned with the person support apparatus.

8 Claims, 11 Drawing Sheets

Related U.S. Application Data

(60) Provisional application No. 62/289,508, filed on Feb. 1, 2016, provisional application No. 62/252,172, filed on Nov. 6, 2015.

(51) Int. Cl.
*A61B 5/11* (2006.01)
*A61G 13/00* (2006.01)
*A61G 13/02* (2006.01)
*A61M 16/04* (2006.01)

(52) U.S. Cl.
CPC ............ *A61B 5/704* (2013.01); *A61B 5/7267* (2013.01); *A61B 5/742* (2013.01); *A61B 5/7405* (2013.01); *A61B 5/746* (2013.01); *A61G 13/0054* (2016.11); *A61G 13/02* (2013.01); *A61G 13/121* (2013.01); *A61M 16/0488* (2013.01); *A61B 2505/05* (2013.01); *A61G 2200/325* (2013.01); *A61G 2203/36* (2013.01)

(58) Field of Classification Search
CPC .......... A61G 13/02; A61G 13/12–1295; A61G 2200/00; A61G 2200/30; A61G 2200/32; A61G 2200/325; A61G 2203/00; A61G 2203/30; A61G 2203/36; A61B 5/704; A61B 2505/00; A61B 2505/05; A61B 5/0059; A61B 5/0077; A61B 5/103; A61B 5/11; A61B 5/1126–1128; A61B 5/70; A61B 5/72; A61B 5/7235; A61B 5/7264; A61B 5/7267; A61B 5/74; A61B 5/7405; A61B 5/742; A61B 5/746; A61M 16/04; A61M 16/0488; A61M 16/0497
See application file for complete search history.

(56) References Cited

U.S. PATENT DOCUMENTS

| | | | |
|---|---|---|---|
| 5,289,520 | A | 2/1994 | Pellegrino et al. |
| 5,707,572 | A | 1/1998 | Kostich |
| 6,279,579 | B1 | 8/2001 | Riaziat et al. |
| 6,311,082 | B1 | 10/2001 | Creighton, IV et al. |
| 7,882,583 | B2 | 2/2011 | Skripps |
| 8,269,825 | B1 * | 9/2012 | Vu ................ A61G 13/121 348/77 |
| 8,648,900 | B2 | 2/2014 | Vu et al. |
| 2004/0097811 | A1 | 5/2004 | Smith et al. |
| 2005/0265516 | A1 | 12/2005 | Haider |
| 2006/0219926 | A1 | 10/2006 | Shoji et al. |
| 2009/0025146 | A1 | 1/2009 | Mazzei et al. |
| 2011/0233415 | A1 | 9/2011 | Nakatsugawa et al. |
| 2014/0161345 | A1 | 6/2014 | Djugash |
| 2017/0035374 | A1 | 2/2017 | Schafer et al. |

FOREIGN PATENT DOCUMENTS

| | | |
|---|---|---|
| EP | 2044880 A1 | 4/2009 |
| WO | 9923990 A1 | 5/1999 |

OTHER PUBLICATIONS

Schaller et al, Time-of-Flight sensor for patient positioning, Proc. SPIE 7261, Medical Imaging 2009: Visualization, Image Guided Procedures, and Modeling, 726110, Mar. 13, 2009.
Extended European Search Report dated Mar. 17, 2017 relating to P Patent Application No. 16196919.1.

* cited by examiner

SUBJECT AND SURGICAL EQUIPMENT MONITORING SYSTEMS

CROSS REFERENCE TO RELATED APPLICATIONS

This application is a division of U.S. patent application Ser. No. 15/343,577 filed Nov. 4, 2016, which claims priority to U.S. Provisional Patent Application Ser. No. 62/252,172 filed Nov. 6, 2015 and entitled "Subject And Surgical Equipment Monitoring Systems" and to U.S. Provisional Patent Application Ser. No. 62/289,508 filed Feb. 1, 2016 and entitled "Subject and Surgical Equipment Monitoring Systems," the entireties are incorporated by reference herein in their entireties.

BACKGROUND

Field

The present specification generally relates to subject and surgical equipment monitoring systems, and more particularly, to systems that monitor positioning of a subject and surgical equipment during a surgical procedure.

Technical Background

In some surgical procedures, such as a spinal procedure, a subject may be positioned in a prone position on a person support apparatus. The subject may be positioned in alignment with features of the person support apparatus that may assist in maintaining the subject in a proper position for the spinal procedure. In some embodiments, the person support apparatus may include a head block including an aperture, and it is desirable to position the eyes of the subject within the aperture during a surgical procedure. When the subject is in the prone position, the subject's eyes are facing downward, and the position of the subject's eyes with respect to the aperture of the head block may be obscured when viewed from above the person support apparatus. As the subject's eyes are obscured, it may be difficult for medical staff to confirm the position of the subject's eyes with respect to the aperture.

Additionally, during a surgical procedure, surgical equipment, such as a breathing tube, may provide air or oxygen to the subject. When the subject is positioned in a prone position on a person support apparatus, the breathing tube may extend from a ventilator and beneath a support deck of the person support apparatus to the subject's mouth. As the breathing tube extends beneath the support deck of the person support apparatus, the positioning of the breathing tube may be obscured when viewed from above the person support apparatus. As the position of the breathing tube is obscured, it may be difficult for medical staff to confirm that the breathing tube is not impinged against the person support apparatus and/or that the breathing tube is connected to the subject.

In some surgical procedures, various objects and surgical equipment may be utilized in conjunction with the person support apparatus. In one example, a C-arm, such as an imaging C-arm, may be moved adjacent to the person support apparatus during a surgical procedure to capture images (i.e., X-rays, CT images, or the like) of the subject during the surgical procedure. When the C-arm is moved toward the person support apparatus, it is desirable to avoid impact between the C-arm and the person support apparatus and/or impact between the C-arm and anesthesia lines, catheter or urinary tubes, neuromonitoring wires, or other similar lines positioned around the person support apparatus.

Accordingly, a need exists for alternative devices for monitoring the positioning of a subject and surgical equipment during a surgical procedure.

SUMMARY

In one embodiment, a surgical monitoring system includes a machine vision sensor, an electronic controller communicatively coupled to the machine vision sensor, the electronic controller including a processor and a memory storing a computer readable instruction set, where, when the computer readable instruction set is executed by the processor, the electronic controller, detects a position of a subject with the machine vision sensor, detects a position of a person support apparatus, compares the detected position of the subject with the detected position of the person support apparatus, and determines if the detected position of the subject and the detected position of the person support apparatus indicates that the subject is not aligned with the person support apparatus.

In another embodiment, a person support apparatus includes a base frame, a primary support frame supported on the base frame, a support deck coupled to the primary support frame, the support deck including a bottom surface, an image capturing device coupled to the base frame, the image capturing device including a field of view that is directed toward the bottom surface of the support deck, and a display unit communicatively coupled to the image capturing device, where the display unit displays images captured by the image capturing device.

In yet another embodiment, a surgical monitoring system includes a machine vision sensor including an image capturing device, the image capturing device including a field of view, an electronic controller communicatively coupled to the machine vision sensor, the electronic controller including a processor and a memory storing a computer readable instruction set, where, when the computer readable instruction set is executed by the processor, the electronic controller detects a position of a person support apparatus, detects a position of an object positioned within the field of view, detects a direction of movement of the object, determines a velocity of the object, and provides an indication if the detected position, the determined velocity, and the detected direction of movement of the object indicate that the object will impact the person support apparatus within a predetermined amount of time.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
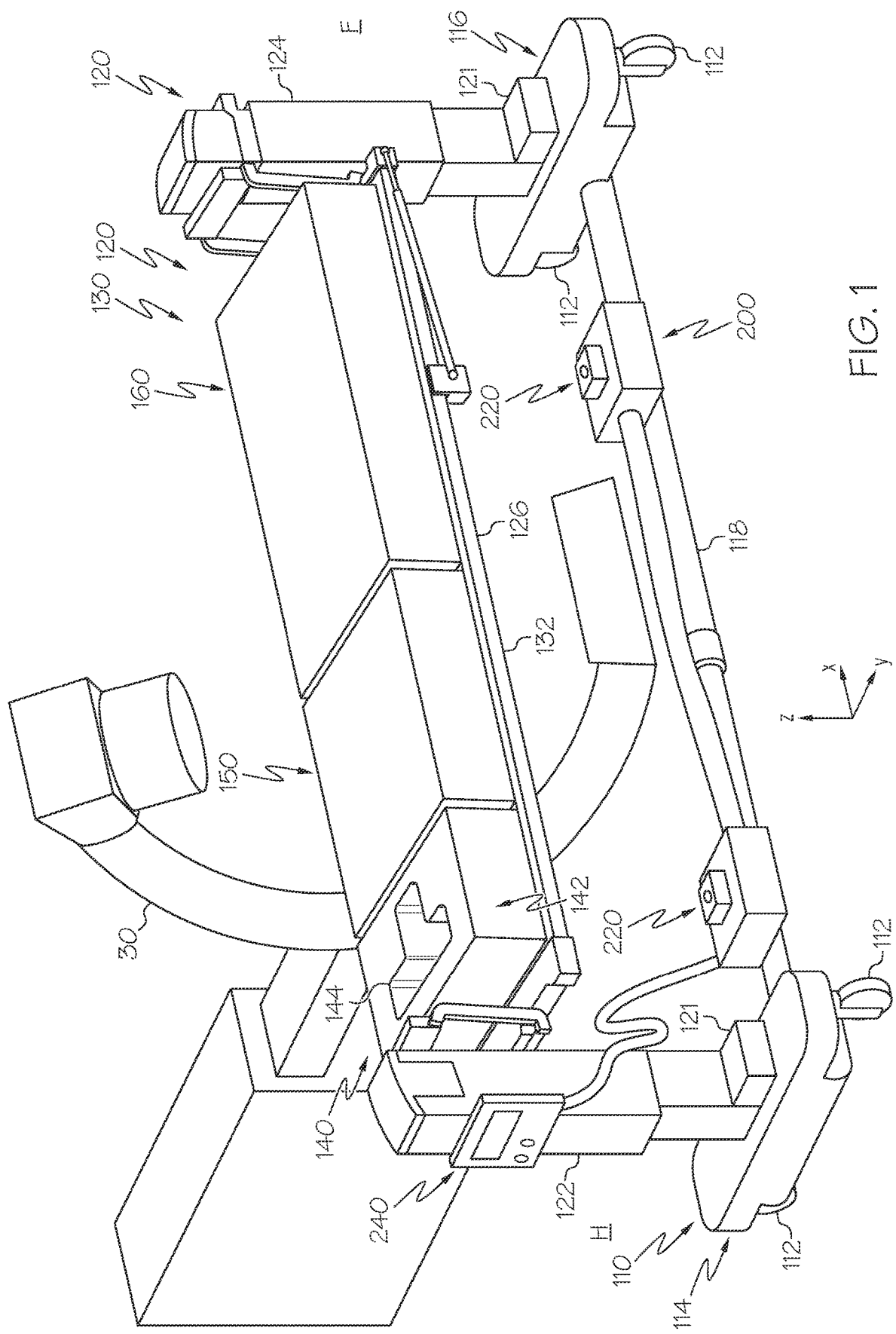
FIG. 1 schematically depicts a perspective view of a person support apparatus including a surgical monitoring system, according to one or more embodiments shown and described herein.

Reference will now be made in detail to embodiments of surgical monitoring systems that monitor positioning of a subject and surgical equipment during a surgical procedure. Whenever possible, the same reference numerals will be used throughout the drawings to refer to the same or like parts. One embodiment of a surgical monitoring system is depicted in FIG. 1 and includes a machine vision sensor positioned on a person support apparatus. The machine vision sensor may detect a position of a subject with respect to the person support apparatus, and provide a signal if the subject is not positioned as desired on the person support apparatus. Additionally or alternatively, the machine vision sensor may detect a position of a breathing tube with respect to the person support apparatus and may detect the position of objects proximate to the person support apparatus, providing a signal if the breathing tube is impinged against the person support apparatus by an object positioned proximate to the person support apparatus. In some embodiments, the vision system detects a position of an object proximate to the person support apparatus, detects a direction of movement and a velocity of the object, and provides a signal if the detected position, the direction of movement, and the velocity of the object indicate an imminent collision between the object and the person support apparatus and/or lines positioned proximate to the person support apparatus. Surgical monitoring systems including machine vision sensors will be described in more detail herein with specific reference to the appended drawings.

As used herein, the term "longitudinal direction" refers to the forward-rearward direction of the person support apparatus (i.e., in the +/−X-direction as depicted). The term "lateral direction" refers to the cross-direction of the person support apparatus (i.e., in the +/−Y-direction as depicted), and is transverse to the longitudinal direction. The term "vertical direction" refers to the upward-downward direction of the person support apparatus (i.e., in the +/−Z-direction as depicted), and is transverse to the lateral and the longitudinal directions. The terms "head end" and "foot end" refer to the relative location of components of the person support apparatus in the longitudinal direction.

The phrase "communicatively coupled" is used herein to describe the interconnectivity of various components of surgical monitoring system and means that the components are directly or indirectly connected either through wires, optical fibers, or wirelessly such that electrical, optical, and/or electromagnetic signals may be exchanged between the components.

Referring to FIG. 1, a person support apparatus 100 is depicted. The person support apparatus 100 may be, for example, a two-column operating table. The person support apparatus 100 generally includes a base frame 110, a primary support frame 120 that is supported by the base frame 110, and a support deck 130 coupled to the primary support frame 120.

The base frame 110 of the person support apparatus 100 includes a forward portion 114 positioned at a head end of the person support apparatus 100 and a rearward portion 116 positioned at a foot end of the person support apparatus 100. The forward portion 114 and the rearward portion 116 are spaced apart from one another in the longitudinal direction and may be coupled to one another through a central portion 118 that extends between the forward portion 114 and the rearward portion 116 in the longitudinal direction. In embodiments, the forward portion 114 and the rearward portion 116 are coupled to a plurality of rollers 112, such that the person support apparatus 100 may be moved along a surface, such as a floor.

In the embodiment depicted in FIG. 1, the primary support frame 120 extends upward from the base frame 110 of the person support apparatus 100 in the vertical direction. In this embodiment, the primary support frame 120 includes a forward column 122 that extends upward from the forward portion 114 of the base frame 110 in the vertical direction. The primary support frame 120 further includes a rearward column 124 that extends upward from the rearward portion 116 of the base frame 110 in the vertical direction. The forward column 122 is positioned at the head end of the person support apparatus 100 and the rearward column 124 is positioned at the foot end of the person support apparatus 100 such that the forward column 122 is spaced apart from the rearward column 124 in the longitudinal direction. In embodiments, the forward column 122 and the rearward column 124 are coupled to the forward portion 114 and the rearward portion 116 of the base frame 110, respectively. Alternatively, the forward column 122 and the rearward column 124 may be integral with the forward portion 114 and the rearward portion 116 of the base frame 110, respectively.

The primary support frame 120 includes a longitudinal frame 126 that is positioned above the base frame 110 in the vertical direction and that extends between the forward column 122 and the rearward column 124 in the longitudinal direction. In the embodiment depicted in FIG. 1, the longitudinal frame 126 generally extends in the horizontal plane (i.e., the X-Y plane as depicted). In other embodiments, the longitudinal frame 126 may be contoured and may include portions that extend out of the horizontal plane. The longitudinal frame 126 supports and may be coupled to the support deck 130, which extends between the forward column 122 and the rearward column 124 in the longitudinal direction.

The forward column 122 and the rearward column 124 may be adjustable in the vertical direction such that the forward column 122 and the rearward column 124 may raise or lower the longitudinal frame 126 with respect to the base frame 110 in the vertical direction. In embodiments, at least one column actuator 121 is coupled to the forward column 122 and/or the rearward column 124 and moves the forward column 122 and the rearward column 124 upward and downward in the vertical direction with respect to the base frame 110. The column actuator 121 may be a powered actuator, such as an electric motor or the like, or may be manually powered, such as by a foot pedal, a crank, or the like. The column actuator 121 may include a linear actuator, such as a screw, a hydraulic actuator, a pneumatic actuator, an electromechanical actuator, or the like.

The forward column 122 and the rearward column 124 may be raised and lowered in the vertical direction independent of one another such that the longitudinal frame 126 may be tilted with respect to the horizontal plane (i.e., the X-Y plane as depicted). For example, the forward column 122 may be raised with respect to the rearward column 124 in the vertical direction such that the head end of the longitudinal frame 126 is positioned higher than the foot end of the longitudinal frame 126 in the vertical direction (i.e., a reverse Trendelenburg position). Conversely, the rearward column 124 may be raised with respect to the forward column 122 in the vertical direction, such that the foot end of the longitudinal frame 126 is positioned higher than the head end of the longitudinal frame 126 in the vertical direction (i.e., a Trendelenburg position). In embodiments, both the forward column 122 and the rearward column 124 of the primary support frame 120 may be raised or lowered in the vertical direction simultaneously, thereby raising both the head end and the foot end of the longitudinal frame 126 with respect to the base frame 110. While the person support apparatus 100 depicted in FIG. 1 is depicted as including a forward column 122 and a rearward column 124 that may be raised and lowered in the vertical direction, it should be understood that person support apparatus 100 may include a single column, or any suitable number of columns, to support the primary support frame 120.

The support deck 130 is positioned on the longitudinal frame 126 and includes one or more segments that are positioned between the forward column 122 and the rearward column 124 in the longitudinal direction to support a subject on the person support apparatus 100. In the embodiment depicted in FIG. 1, the support deck 130 includes an upper segment 140 positioned at the head end of the person support apparatus 100 which supports the upper body and/or the head and arms of a subject. The support deck 130 may further include a leg segment 160 positioned at the foot end of the person support apparatus 100, and a torso segment 150 that is positioned between the upper segment 140 and the leg segment 160 in the longitudinal direction.

Each of the upper segment 140, the torso segment 150, and the leg segment 160 include generally planar surfaces that support a subject on the person support apparatus 100. In some embodiments, the upper segment 140, the torso segment 150, and/or the leg segment 160 may include contoured or shaped surfaces that accommodate a subject.

Figure 2:
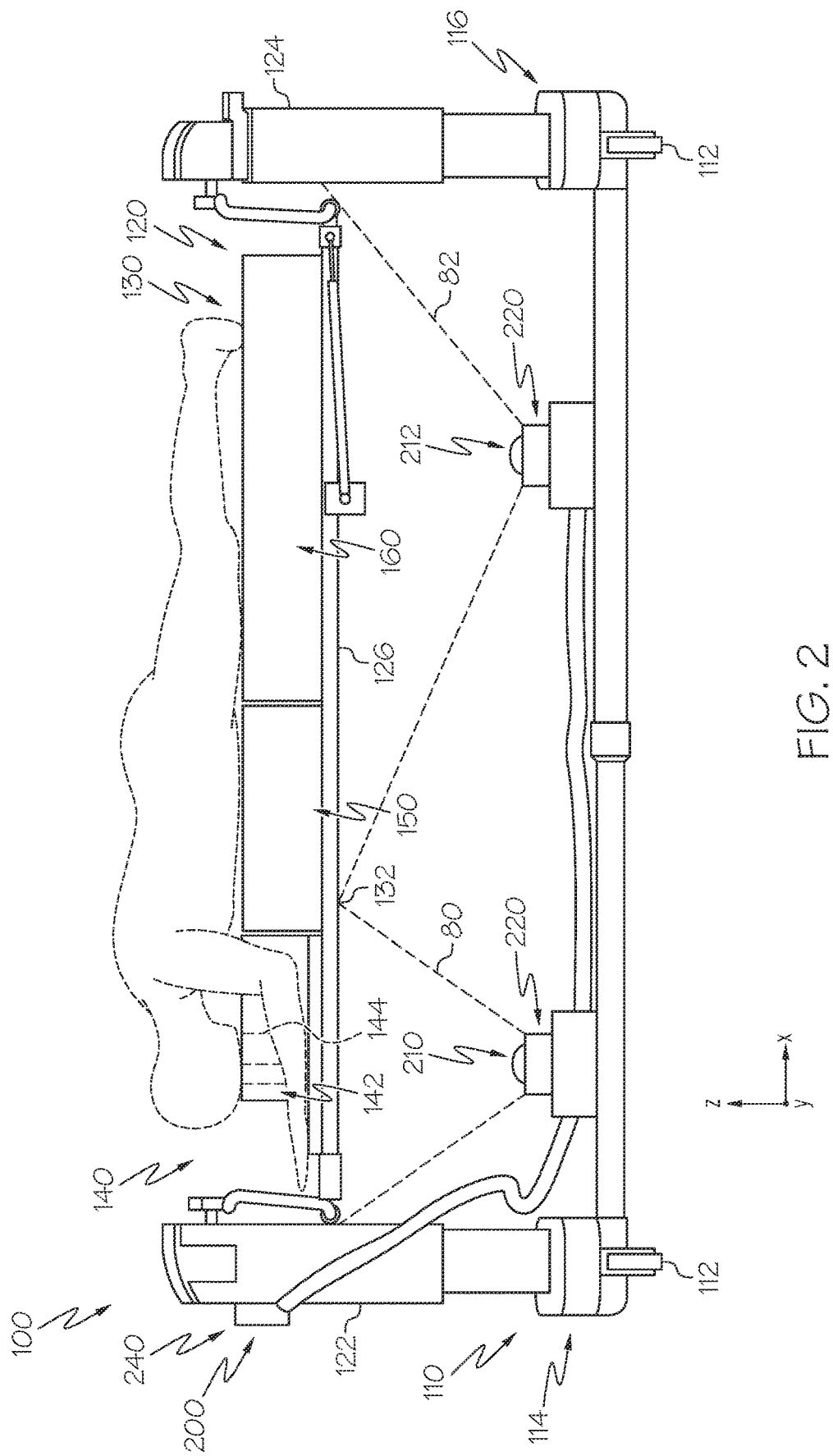
FIG. 2 schematically depicts a side view of the person support apparatus and the surgical monitoring system of FIG. 1, according to one or more embodiments shown and described herein.

Referring collectively to FIGS. 1 and 2, the upper segment 140 includes a head block 142. The head block 142 may assist in supporting a subject's head on the person support apparatus 100, and may be formed from materials such as polyurethane foam, or the like. The head block 142 defines a t-shaped aperture 144 that extends through the head block 142, which may accommodate the eyes, nose, and/or mouth of a subject when the subject is in a prone position on the person support apparatus 100, as will be described in greater detail herein.

In the embodiments described herein, a surgical monitoring system 200 is positioned on the person support apparatus 100. The surgical monitoring system 200 includes a machine vision sensor 220, an electronic controller 230 (FIG. 4) communicatively coupled to the machine vision sensor 220, and a display unit 240 communicatively coupled to the electronic controller 230.

The display unit 240 includes a pendant that is communicatively coupled to the machine vision sensor 220 by a tether or wire. Alternatively, the display unit 240 may be communicatively coupled to the machine vision sensor 220 through a wireless connection. In the embodiment depicted in FIGS. 1 and 2, the display unit 240 is removably coupled to the forward column 122 of the person support apparatus 100 such that the display unit 240 may be selectively removed from the person support apparatus 100. Alternatively, the display unit 240 may be integral with or rigidly coupled to the person support apparatus 100.

Figure 3:
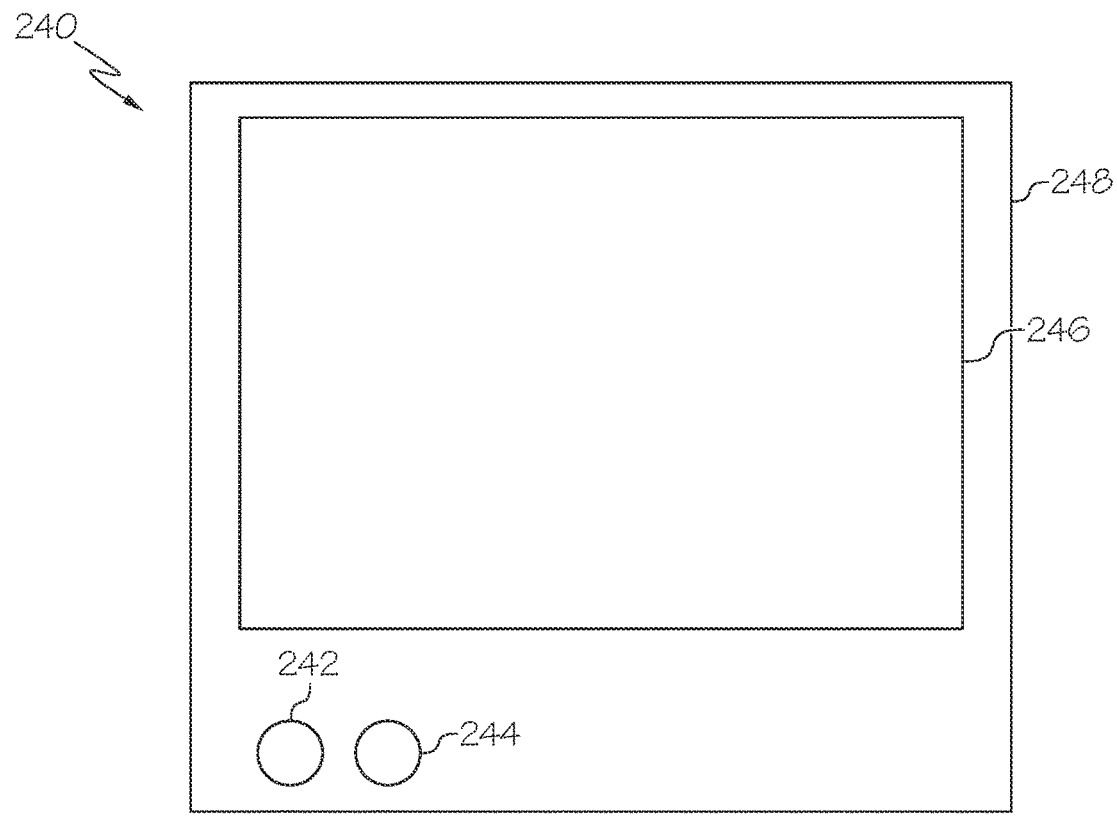
FIG. 3 schematically depicts a display unit of the surgical monitoring system of FIG. 1, according to one or more embodiments shown and described herein.

Referring to FIG. 3, the display unit 240 of the surgical monitoring system 200 is depicted in isolation. The display unit 240 includes a visual indicator 242, an audible indicator 244, and a visual display 246 positioned on a housing 248. The visual indicator 242, the audible indicator 244, and/or the visual display 246 selectively provide an audible and/or visual signal, such as a warning signal, based on conditions detected by the machine vision sensor 220, as will be described in greater detail herein.

The visual indicator 242 includes an illumination device, including, but not limited to, a light emitting diode (LED), a fluorescent lamp, an incandescent lamp, or any other suitable light source. The audible indicator 244 includes an acoustic transducer that may include an electromechanical element that converts electrical energy into mechanical energy, such as a speaker, or the like. The visual display 246 of the display unit includes a display screen that may show images captured by the machine vision sensor 220. In embodiments, the display screen of the visual display 246 may include a liquid crystal display (LCD), a light emitting diode (LED) display, a gas-plasma display, or any other suitable display. In some embodiments, the visual display 246 includes a graphical user interface (GUI) and may include a screen that accepts a user input, such as a capacitive touch screen, a resistive touch screen, or the like. In these embodiments, the visual display 246 may show images captured by the machine vision sensor 220 and may also detect user inputs to the touch screen to control various functions of the person support apparatus 100, such as raising or lowering the support deck 130 in the vertical direction.

Referring again to FIG. 2, the machine vision sensor 220 is coupled to the base frame 110 of the person support apparatus 100. In the embodiment depicted in FIG. 2, the machine vision sensor 220 includes a first image capturing device 210 and a second image capturing device 212 positioned beneath the support deck 130 and directed toward the bottom surface 132 of the support deck 130. The first image capturing device 210 is positioned at the head end of the person support apparatus 100 and the second image capturing device 212 is positioned at the foot end of the person support apparatus. The first image capturing device 210 and the second image capturing device 212 include devices, such as cameras, that capture still images and/or video. The first image capturing device 210 includes a field of view 80, such that the first image capturing device 210 captures an image of the bottom surface 132 of the support deck 130, and, in particular, the aperture 144 of the upper segment 140 and/or the head block 142. By directing the first image capturing device 210 toward the aperture 144 of the upper segment 140 and/or head block 142, the first image capturing device 210 may capture an image indicating a position of a subject relative to the aperture 144, as will be described in greater detail herein. The second image capturing device 212 includes a field of view 82, such that the second image capturing device 212 captures an image of the bottom surface 132 of the support deck 130, and, in particular the bottom surface 132 of the torso segment 150 and/or the leg segment 160. While the surgical monitoring system 200 is depicted and described as including a first image capturing device 210 and a second image capturing device 212, it should be understood that the surgical monitoring system 200 may include a single image capturing device or any suitable number of image capturing devices to capture an image of the bottom surface 132 of the support deck 130 along the length of the person support apparatus 100. In some embodiments, the surgical monitoring system 200 may include any suitable number of image capturing devices to detect movement and positioning of objects positioned proximate to the person support apparatus 100 in the longitudinal direction, the lateral direction, and the vertical direction, as will be described in greater detail herein.

Figure 4:
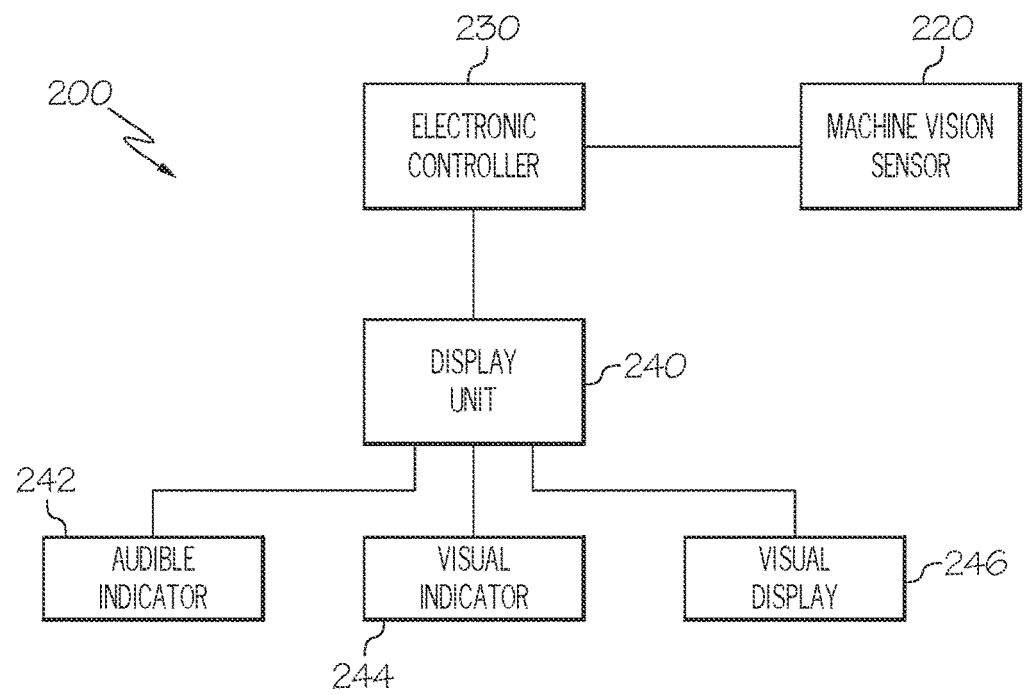
FIG. 4 schematically depicts a block diagram of the interconnectivity of an electronic controller, a machine vision sensor, and the display unit of the surgical monitoring system of FIG. 1 according to one or more embodiments shown and described herein.

Referring to FIG. 4, a block diagram of the interconnectivity of the electronic controller 230, the machine vision sensor 220, and the display unit 240 of the surgical monitoring system 200 is schematically depicted. The machine vision sensor 220 and the display unit 240 are communicatively coupled to the electronic controller 230. In embodiments, the electronic controller 230 is integral with one of the machine vision sensor 220 and the display unit 240, and the electronic controller 230 is communicatively coupled to the other of the machine vision sensor 220 and the display unit 240. Alternatively, the electronic controller 230 may be a standalone controller that is communicatively coupled to both the machine vision sensor 220 and the display unit 240. The electronic controller includes a processor and a memory storing a computer readable instruction set which, when executed by the processor facilitates operation of the surgical monitoring system 200, as will be described in greater detail herein.

Figure 5A:
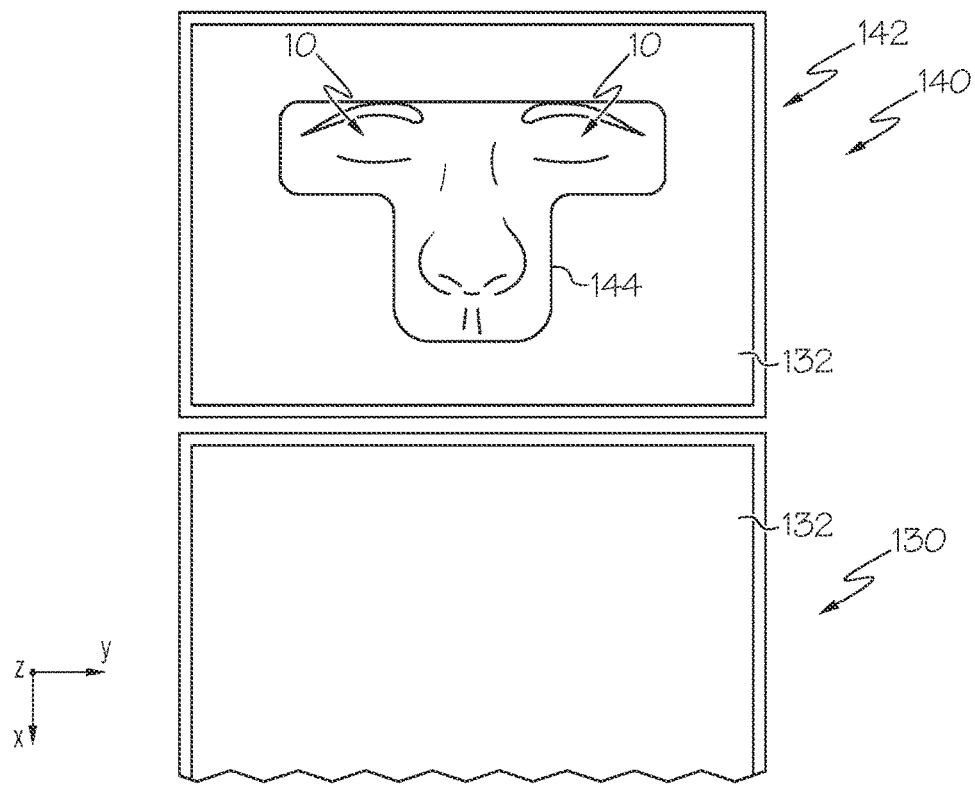
FIG. 5A schematically depicts a bottom view of a subject on the person support apparatus of FIG. 1 according to one or more embodiments shown and described herein.

Referring to FIG. 5A, a bottom view of the person support apparatus 100, such as may be captured by the first image capturing device 210, is depicted. When a subject is positioned on the person support apparatus 100 in a prone position, the subject's head may be positioned on the upper segment 140 such that the eyes 10 of the subject are positioned within the aperture 144 of the head block 142 in the longitudinal and lateral directions. When the subject is positioned on the person support apparatus 100 in a prone position, it is desirable to position the eyes 10 of the subject within the aperture 144 of the head block 142, as shown in FIG. 5A, to align the subject with the person support apparatus 100 and to position the subject's head for a surgical procedure, such as a spinal procedure.

Figure 5B:
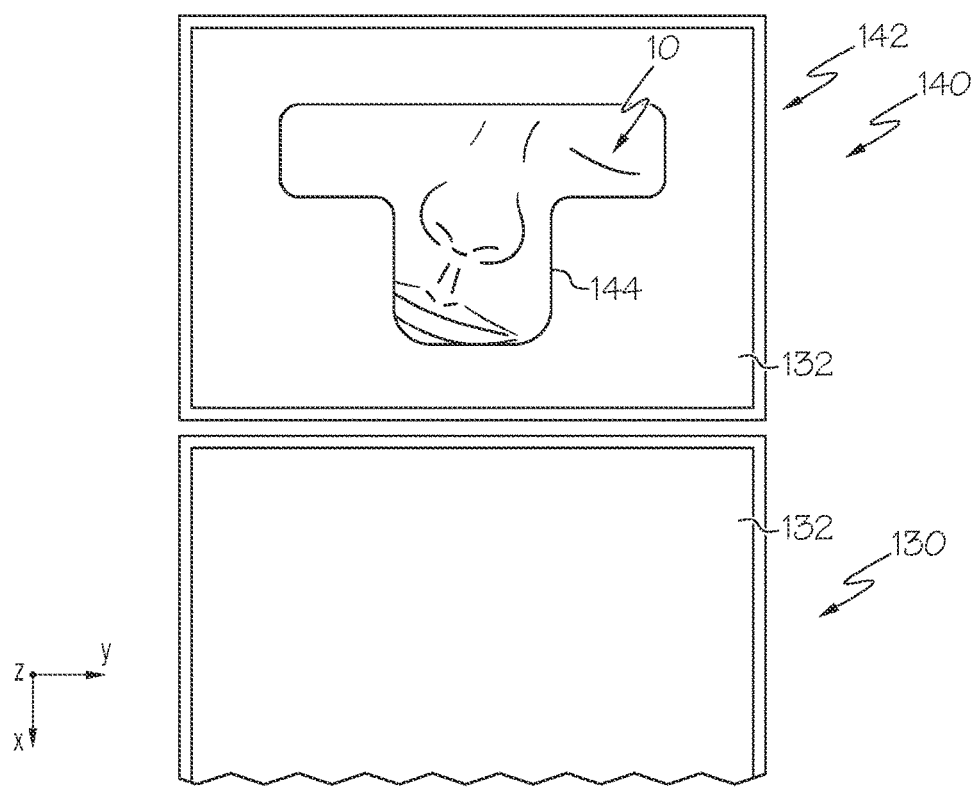
FIG. 5B schematically depicts another bottom view of a subject on the person support apparatus of FIG. 1 according to one or more embodiments shown and described herein.

Referring to FIG. 5B, another bottom view of the person support apparatus 100, such as may be captured by the first image capturing device 210, is depicted. In some instances, when the subject is positioned on the person support apparatus 100, the subject's head may be positioned on the upper segment 140 such that one or both of the eyes 10 of the subject are not positioned within the aperture 144 in the longitudinal and lateral directions, as shown in FIG. 5B. When the eyes 10 of the subject are positioned outside or at least partially outside of the aperture 144, the subject's head may not be positioned appropriately for surgery, and it may be desirable to reposition and align the subject with the person support apparatus 100 such that the eyes 10 of the subject are positioned within the aperture 144.

Referring collectively to FIGS. 5A and 5B, the electronic controller 230 (FIG. 4) includes an object recognition module stored in memory that stores an image indicative of the bottom surface 132 of the support deck 130 and the aperture 144, such that the electronic controller 230 may identify the aperture 144 from an image captured by the first image capturing device 210 (FIG. 2). The electronic controller 230 (FIG. 4) further includes an object recognition module stored in memory that stores an image indicative of the eyes 10 of a subject, such that the electronic controller 230 may identify the eyes 10 of a subject from an image captured by the first image capturing device 210 (FIG. 2) and/or the second image capturing device 212 (FIG. 2). While images of the eyes 10 of different subjects may vary, the parameters of the object recognition module may broadly identify the eyes 10 of different subjects distinguished from other facial features of the subject and distinguished from the person support apparatus 100. In some embodiments, the electronic controller 230 may detect and identify the eyes 10 of the subject while a bandage and/or tape is positioned over the eyes of the subject. By storing an image indicative of the aperture 144 and an image indicative of the eyes 10 of a subject, the electronic controller 230 may identify and compare detected positions of the aperture 144 and the eyes 10 of the subject, such that the surgical monitoring system 200 may provide an indication with the visual indicator 242, the audible indicator 244, and/or the visual display 246, based on the detected positions of the aperture 144 and the eyes 10 of the subject, as will be described in greater detail herein.

Figure 6A:
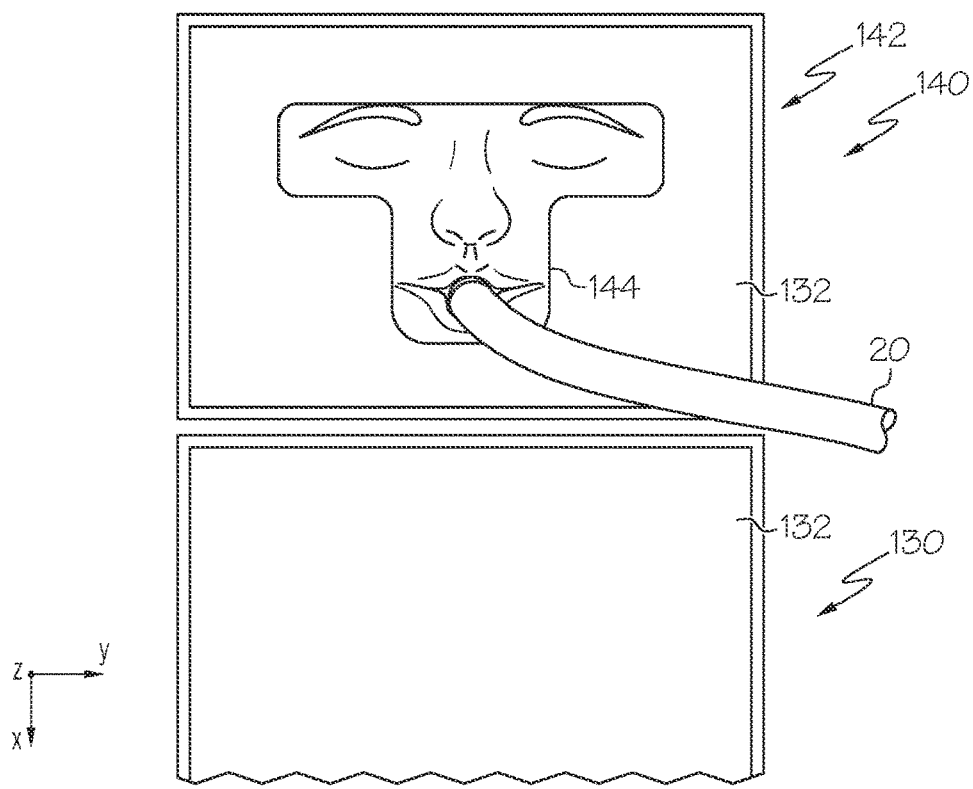
FIG. 6A schematically depicts a bottom view of a breathing tube under the person support apparatus of FIG. 1 according to one or more embodiments shown and described herein.

Referring to FIG. 6A, another bottom view of the person support apparatus 100, such as may be captured by the first image capturing device 210, is depicted. A breathing tube 20 is positioned beneath the person support apparatus 100 and may extend across at least a portion of the support deck 130 of the person support apparatus 100. In some embodiments, the breathing tube 20 may include an endotracheal tube that is coupled to a ventilator (not depicted) to provide air or oxygen to a subject during a surgical procedure. During a surgical procedure, it is desirable that the breathing tube 20 is not impinged against the person support apparatus 100 or any other objects proximate to the person support apparatus 100, such that the breathing tube 20 may provide air or oxygen to the subject without impediment.

Figure 6B:
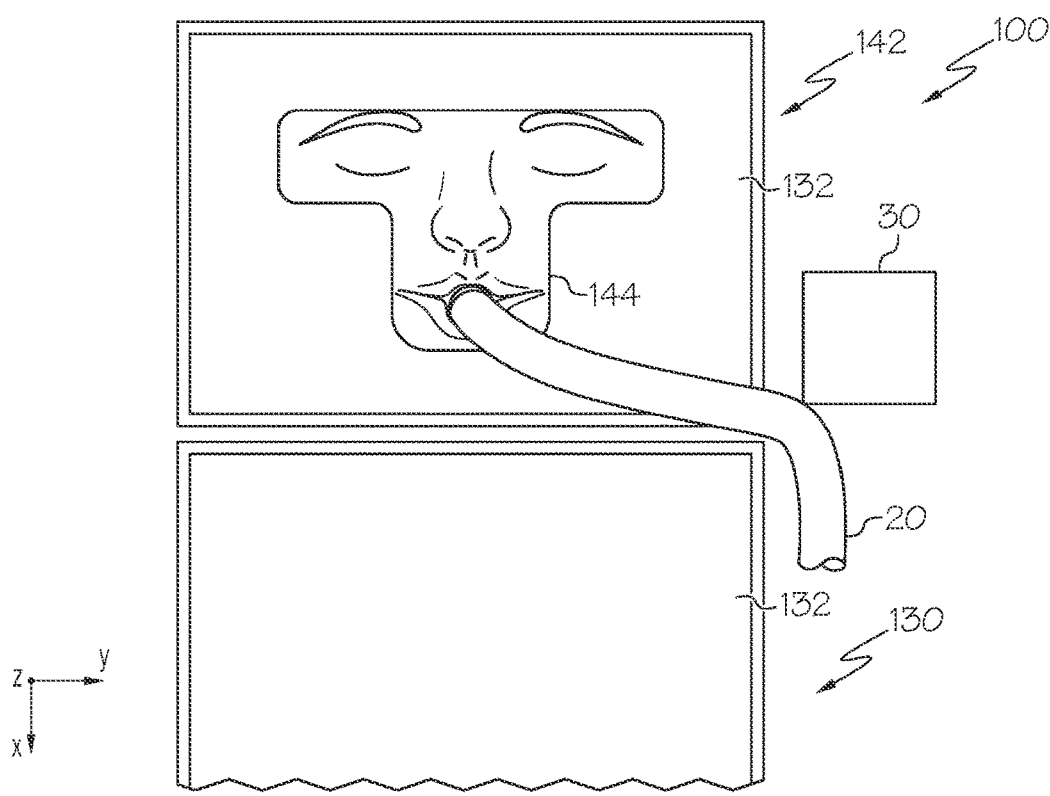
FIG. 6B schematically depicts another bottom view of a breathing tube under the person support apparatus of FIG. 1 according to one or more embodiments shown and described herein.

Referring to FIG. 6B, another bottom view of the person support apparatus 100, such as may be captured by the first image capturing device 210, is depicted. In some instances, the breathing tube 20 may be impinged between the person support apparatus 100 and an object 30, as shown in FIG. 6B. As shown in FIG. 6B, the breathing tube 20 is positioned between the object 30 and the support deck 130 in the lateral direction, and is impinged between the object 30 and the support deck 130 of the person support apparatus 100. The object 30 is depicted as a rectangular body, but may include any one of various objects that may be positioned proximate to the person support apparatus 100 during a surgical procedure, such as a C-arm, a table, or other object positioned in the operating room. When the breathing tube 20 is impinged against the person support apparatus 100, it is desirable to reposition breathing tube 20 and/or the object 30 such that breathing tube 20 is not impinged against the person support apparatus 100 and air or oxygen is provided to the subject without impediment.

Referring collectively to FIGS. 6A and 6B, the electronic controller 230 (FIG. 4) includes an object recognition module stored in memory that stores an image indicative of the bottom surface 132 of the support deck 130 and the breathing tube 20, as shown in FIGS. 6A and 6B. By storing an image indicative of the bottom surface 132 of the support deck 130 and an image of the breathing tube 20, the electronic controller 230 (FIG. 4) may distinguish the breathing tube 20 and bottom surface 132 of the support deck 130 from another object 30 or objects in an image captured by the first image capturing device 210 (FIG. 2) and/or the second image capturing device 212 (FIG. 2). By identifying the object 30 or objects, the electronic controller 230 (FIG. 4) may detect a position of the object 30, the breathing tube 20, and the person support apparatus 100, and provide an indication if the detected positions of the object 30, the breathing tube 20, and the person support apparatus 100 indicate that the breathing tube 20 is impinged against the person support apparatus 100, as will be described in greater detail herein.

Figure 7A:
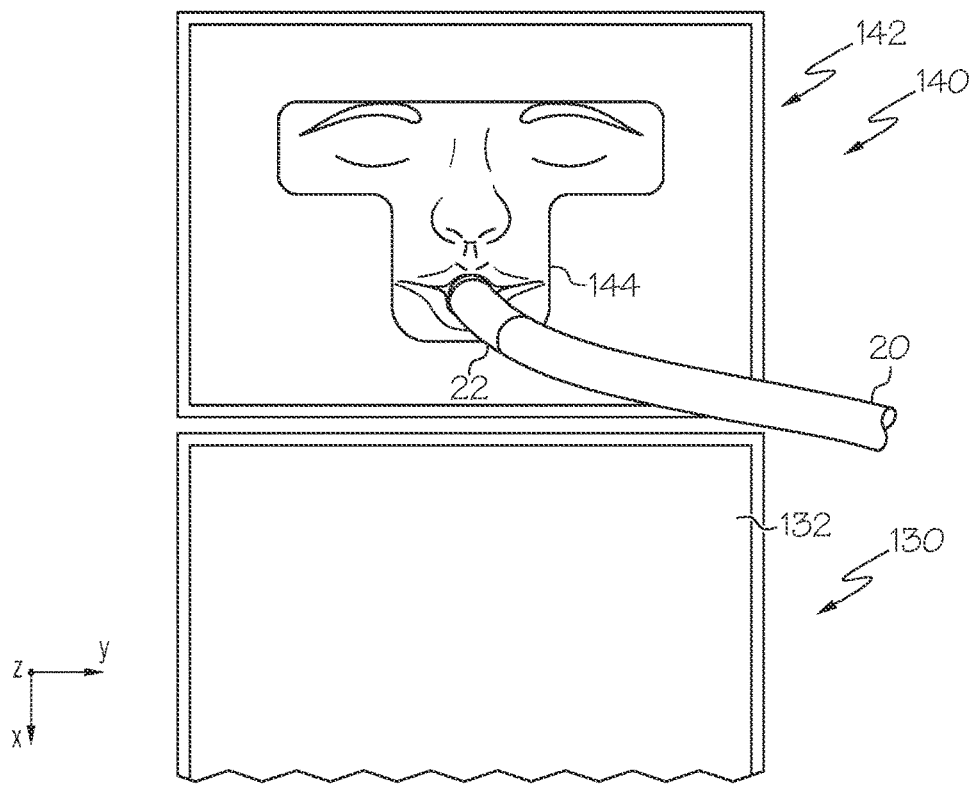
FIG. 7A schematically depicts a bottom view of a breathing tube under the person support apparatus of FIG. 1 according to one or more embodiments shown and described herein.

Referring to FIG. 7A, another bottom view of the person support apparatus 100, such as may be captured by the first image capturing device 210, is depicted. The breathing tube 20 is positioned beneath the person support apparatus 100 and may extend across at least a portion of the support deck 130 of the person support apparatus 100. In the embodiment depicted in 7A, the breathing tube 20 is coupled to an endotracheal tube 22. During a surgical procedure, it is desirable that the breathing tube 20 remains coupled to the endotracheal tube 22, such that the breathing tube 20 may provide air or oxygen to the subject without impediment.

Figure 7B:
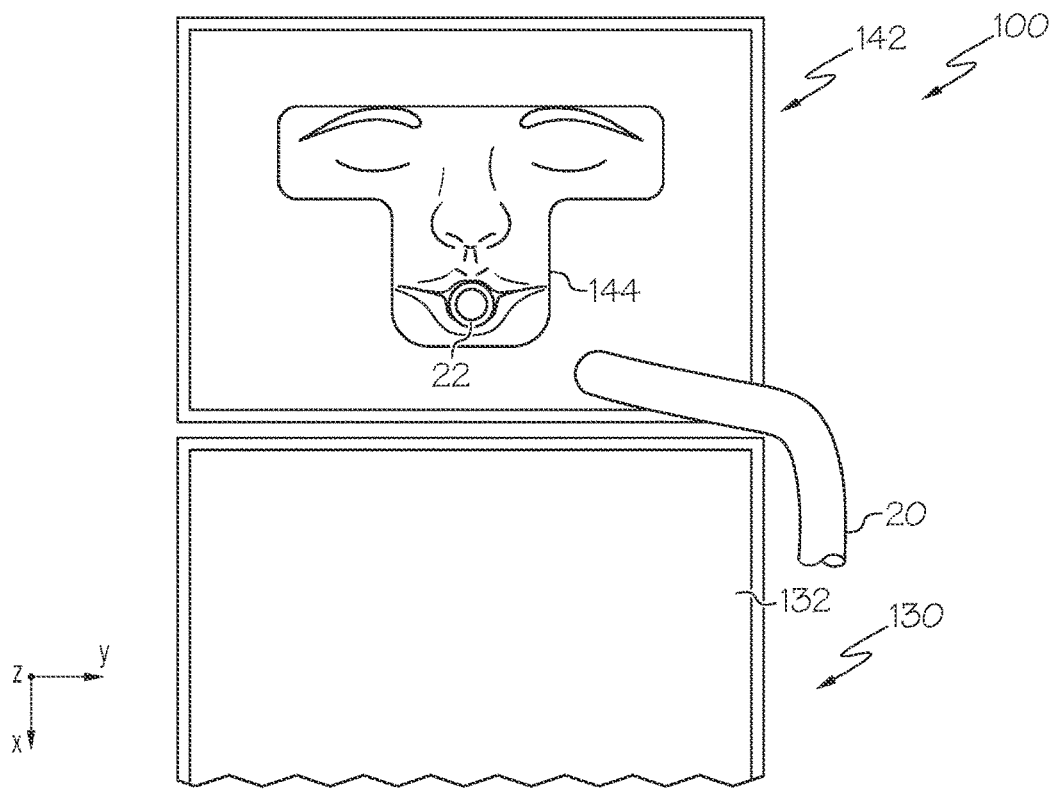
FIG. 7B schematically depicts another bottom view of a breathing tube under the person support apparatus of FIG. 1 according to one or more embodiments shown and described herein.

Referring to FIG. 7B, another bottom view of the person support apparatus 100, such as may be captured by the first image capturing device 210, is depicted. In some instances, the breathing tube 20 may become decoupled from the endotracheal tube 22. As shown in FIG. 7B, the breathing tube 20 is decoupled from the endotracheal tube 22. When the breathing tube 20 is decoupled from the endotracheal tube 22, it is desirable to couple the breathing tube 20 to the endotracheal tube 22 so that air or oxygen is provided to the subject without impediment.

Referring collectively to FIGS. 7A and 7B, the electronic controller 230 (FIG. 4) includes an object recognition module stored in memory that stores an image indicative of the breathing tube 20 and the endotracheal tube 22, as shown in FIGS. 7A and 7B. By storing an image indicative of the breathing tube 20 and the endotracheal tube 22, the electronic controller 230 (FIG. 4) may detect if the breathing tube 20 is decoupled from the endotracheal tube 22 in an image captured by the first image capturing device 210 (FIG. 2) and/or the second image capturing device 212 (FIG. 2). The electronic controller 230 (FIG. 4) may provide an indication if the breathing tube 20 is decoupled from the endotracheal tube 22, as will be described in greater detail herein.

Figure 8:
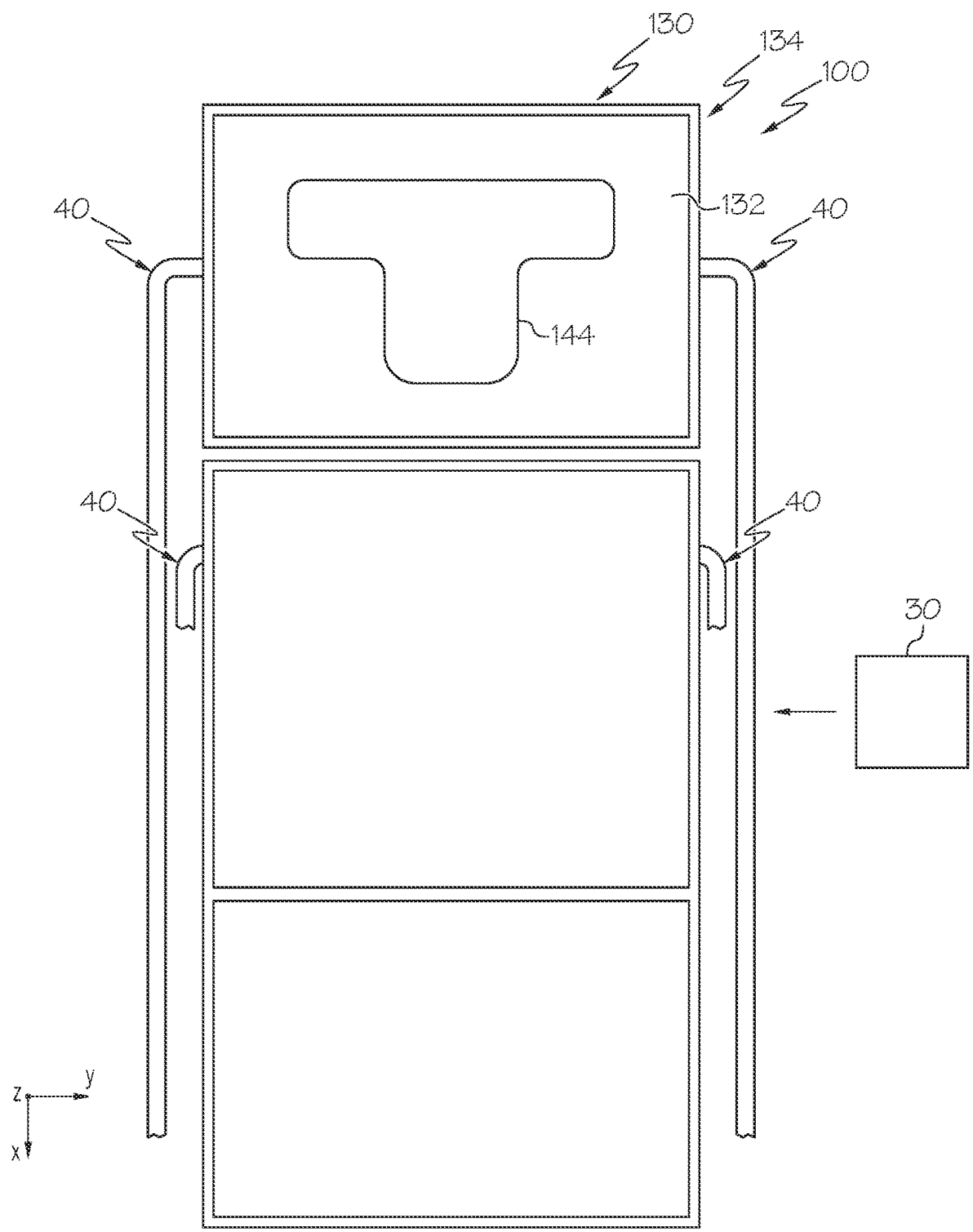
FIG. 8 schematically depicts a bottom view of the person support apparatus of FIG. 1 and an object moving toward the person support apparatus according to one or more embodiments shown and described herein.

Referring to FIG. 8, another bottom view of the person support apparatus 100, such as may be captured by the first image capturing device 210 and/or the second image capturing device 212, is depicted. During a surgical procedure, various lines 40, such as anesthesia lines, neuromonitoring wires, a foley catheter, urinary lines, or the like, may be coupled to the subject. In some embodiments, the lines 40 may include the breathing tube 20 (FIG. 6A). When the subject is positioned on the support deck 130, the lines 40 may extend from the subject and may be positioned proximate to the person support apparatus 100. In the embodiment depicted in FIG. 8, the lines 40 are draped over a perimeter 134 of the person support apparatus 100, extending at least partially downward from the support deck 130 in the vertical direction.

In some instances, an object 30, such as a C-arm or other piece of surgical equipment, may be moved adjacent to the person support apparatus 100 during a surgical procedure. In one example, when the object 30 includes a C-arm, the C-arm may be moved adjacent to the person support apparatus 100 to capture images of the subject, such as X-rays, CT images, or the like. As shown in FIG. 8, the object 30 is being moved toward the person support apparatus 100 in the lateral direction. While the surgical equipment may be moved toward or around the person support apparatus 100 during a surgical procedure, it is desirable that the object 30 does not impact the person support apparatus 100 or the lines 40 positioned proximate to the person support apparatus 100.

To detect or assist in preventing impact, the electronic controller 230 (FIG. 4) includes an object recognition module stored in memory that stores an image indicative of the person support apparatus 100 and the lines 40 as shown in FIG. 7. While the lines 40 may be positioned in a variety of orientations around the person support apparatus 100, the parameters of the object recognition module may broadly identify the lines 40 as distinguished from the person support apparatus 100. By storing an image indicative of the person support apparatus 100 and the lines 40, the electronic controller 230 (FIG. 4) may distinguish the person support apparatus 100 and the lines 40 from another object 30 or objects in an image captured by the first image capturing device 210 (FIG. 2) and/or the second image capturing device 212 (FIG. 2). As the electronic controller 230 (FIG. 4) distinguishes the object 30 from the lines 40 and the person support apparatus 100, the electronic controller 230

(FIG. 4) may determine a position of the object 30 relative to the person support apparatus 100 and/or the lines 40 in the lateral and longitudinal directions. When the object 30 is moving in the lateral and/or the longitudinal direction, the electronic controller 230 (FIG. 4) may determine a direction of motion and velocity of the object 30 with respect to the person support apparatus 100 and/or the lines 40 based on the detected position of the object 30 with respect to the person support apparatus 100 and/or the lines 40 in successive images captured by the first image capturing device 210 (FIG. 2) and/or the second image capturing device 212 (FIG. 2).

When the detected position of the object 30, and the detected direction of motion and velocity of the object 30 indicate that the object will imminently impact the person support apparatus 100 and/or the lines 40, the electronic controller 230 (FIG. 4) may provide an indication that an impact is imminent. In embodiments, the electronic controller 230 (FIG. 4) provides an indication if the detected position, velocity, and direction of motion of the object 30 indicates that the object will impact the person support apparatus 100 and/or the lines 40 in less than 5 seconds. In other embodiments, the electronic controller 230 (FIG. 4) provides an indication if the detected position, velocity, and direction of motion of the object 30 indicates that the object will impact the person support apparatus 100 and/or the lines 40 in less than 3 seconds. In still other embodiments, the electronic controller 230 (FIG. 4) provides an indication if the detected position, velocity, and direction of motion of the object 30 indicates that the object will impact the person support apparatus 100 and/or the lines 40 in less than 1 second.

In some embodiments, the surgical monitoring system 200 may detect movement of any one of the lines 40 based on a detected position of the lines 40 in successive images captured by the first image capturing device 210 (FIG. 2) and/or the second image capturing device 212 (FIG. 2). In particular, the surgical monitoring system 200 may detect an initial position of the line 40 and may detect a subsequent position of the line 40 in a successive image. The electronic controller 230 determines the distance between the initial position and the subsequent position, which is indicative of the movement of the line 40. Regardless of whether an imminent impact is detected between the lines 40 and an object 30, movement of any of the lines 40 may indicate that force is being applied to the lines 40, which may result in the lines 40 being decoupled from the subject. Accordingly, it is desirable to limit movement of the lines 40 and to provide an indication with the visual indicator 242 (FIG. 4), the audible indicator 244 (FIG. 4), and/or the visual display 246 (FIG. 4) if movement of the lines 40 greater than a predetermined distance is detected.

In embodiments, the electronic controller 230 provides an indication if any one of the lines 40 moves more than 7 centimeters (cm) in the longitudinal direction, the lateral direction, and/or the vertical direction between an initial position and a subsequent position. In another embodiment, the electronic controller 230 provides an indication if any one of the lines 40 moves more than 5 cm in the longitudinal direction, the lateral direction, and/or the vertical direction between an initial position and a subsequent position. In yet another embodiment, the electronic controller 230 provides an indication if any one of the lines 40 moves more than 2 cm in the longitudinal direction, the lateral direction, and/or the vertical direction between an initial position and an subsequent position. By providing an indication based on the detected movement of any of the lines 40, the electronic controller 230 may assist medical staff in identifying excessive movement of the lines that may result in the lines being decoupled from the subject.

Referring collectively to FIGS. 3, 5A, 5B, 6A, 6B, 7A, 7B, and 8, images captured by the first image capturing device 210 and/or the second image capturing device 212 of the bottom surface 132 of the support deck 130 may be presented on the visual display 246. In particular, images capture by the first image capturing device 210 and/or the second image capturing device 212 may be communicated to the visual display 246, for example, through the electronic controller 230 (FIG. 4), and the images may be presented on the visual display 246. The visual display 246 may show images captured by the first image capturing device 210 and/or the second image capturing device 212 showing the position of the subject's eyes 10 with respect to the aperture 144, as shown in FIGS. 5A and 5B. Likewise, the visual display 246 may show images captured by the first image capturing device 210 and/or the second image capturing device 212 showing the position of the breathing tube 20, as shown in FIGS. 6A and 6B. Similarly, the visual display 246 may show images captured by the first image capturing device 210 and/or the second image capturing device 212 showing the breathing tube 20 coupled to or decoupled from the endotracheal tube 22, as shown in FIGS. 7A and 7B. By presenting images captured by the first image capturing device 210 and/or the second image capturing device 212 on the visual display 246, users, such as medical support staff, can view the positioning of a subject with respect to the person support apparatus 100 and the positioning of the breathing tube 20 during a surgical procedure, and can reposition the subject, the person support apparatus 100, and/or the breathing tube 20 as desired.

As described above, the surgical monitoring system 200 includes a machine vision sensor 220 that selectively provides indications with the visual indicator 242, the audible indicator 244, and/or the visual display 246 based on inputs to the machine vision sensor 220. Methods for operating the surgical monitoring system 200 will now be described with specific reference to the figures.

Figure 9:
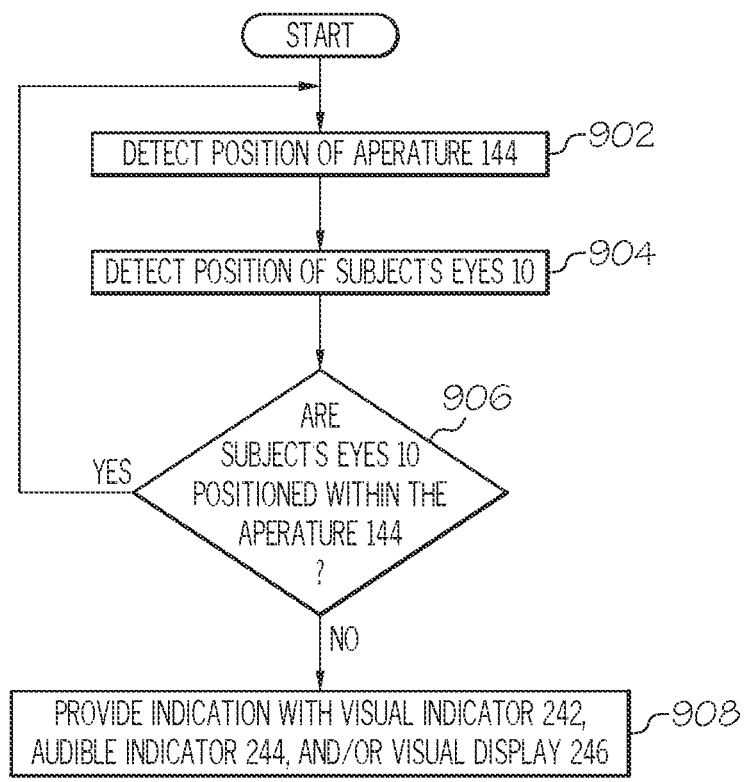
FIG. 9 schematically depicts a flowchart for one method of operating the surgical monitoring system of FIG. 1 according to one or more embodiments shown and described herein.

Referring to FIGS. 1, 4, 5A, 5B, and 9, one embodiment of a method of operating the surgical monitoring system 200 is depicted in the flowchart of FIG. 9. In a first step 902, the machine vision sensor 220 detects a position of the aperture 144 of the head block 142. In a second step 904, the machine vision sensor 220 detects a position of the eyes 10 of a subject. At step 906, the electronic controller 230 determines if the eyes 10 of the subject are positioned within the aperture 144 based on the detected position of the eyes 10 of the subject and the detected position of the aperture 144. If the detected position of at least one of the eyes 10 of the subject is not positioned within the aperture 144, the electronic controller 230 proceeds to step 908, where the electronic controller 230 provides an indication with the visual indicator 242, the audible indicator 244, and/or the visual display 246. If the detected positions of the eyes 10 of the subject are within the detected position of the aperture 144, the electronic controller 230 proceeds back to step 902, repeating the process.

While the steps of the detection of the position of the aperture 144 (step 902) and the detection of the position of the eyes 10 of the subject (step 904) are described in a specific order in the embodiment described and depicted in FIG. 9, it should be understood that these steps may be performed in any order or may be performed simultaneously. As described above, it is desirable that the subject is aligned with the person support apparatus 100, and that the eyes 10 of the subject are positioned within the aperture 144 of the head block 142 to position the subject for some surgical procedures. Accordingly, by providing an indication when the detected position of the eyes 10 of the subject is not within the aperture 144, the surgical monitoring system 200 may assist medical staff in identifying when a subject is not positioned as desired with respect to the person support apparatus 100.

Figure 10:
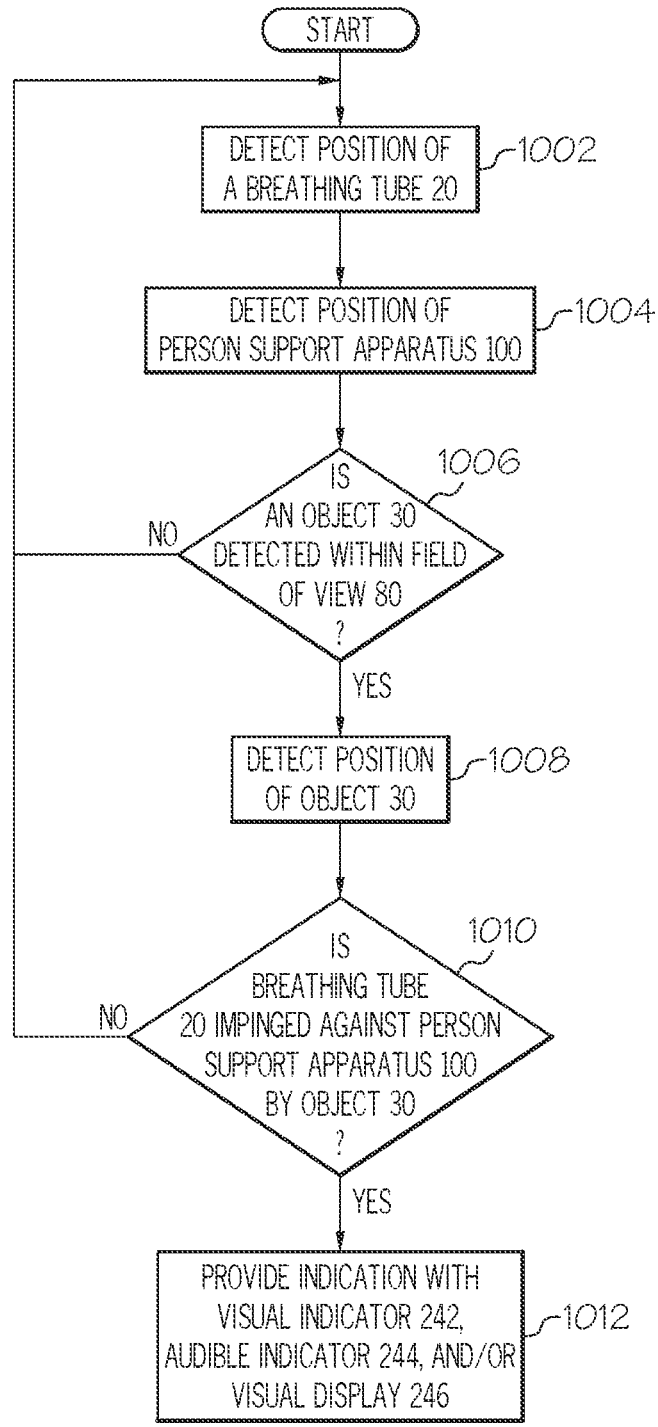
FIG. 10 schematically depicts another flowchart for one method of operating the surgical monitoring system of FIG. 1 according to one or more embodiments shown and described herein.

Referring to FIGS. 1, 4, 6A, 6B, and 10, another embodiment of a method of operating the surgical monitoring system 200 is depicted in the flowchart of FIG. 10. In a first step 1002, the machine vision sensor 220 detects a position of a breathing tube 20. In a second step 1004, the machine vision sensor 220 detects a position of the person support apparatus 100. In a third step 1006, the machine vision sensor 220 detects if an object 30 is positioned within a field of view 80 of the first image capturing device 210 and/or the field of view 82 of the second image capturing device 212 of the machine vision sensor 220. If an object 30 is not detected within the field of view 80, 82 of the machine vision sensor 220, the electronic controller 230 returns to step 1002. If an object 30 is detected within the field of view 80, 82 of the machine vision sensor 220, the electronic controller 230 proceeds to step 1008 and determines a position of the object 30. The electronic controller 230 then proceeds to step 1010, and determines if the breathing tube 20 is impinged against the person support apparatus 100 by the object 30 based on the detected position of the breathing tube 20, the detected position of the person support apparatus 100, and the detected position of the object. If the detected position of the breathing tube 20, the detected position of the person support apparatus 100, and the detected position of the object 30 indicates that the breathing tube 20 is impinged against the person support apparatus 100 by the object 30, the electronic controller 230 proceeds to step 1012, where the electronic controller 230 provides an indication with the visual indicator 242, the audible indicator 244, and/or the visual display 246. If the detected positions of the breathing tube 20, the detected position of the person support apparatus 100, and the detected position of the object 30 indicate that the breathing tube 20 is not impinged against the person support apparatus 100, the electronic controller 230 proceeds back to step 1002, repeating the process.

While the steps of detecting the position of the breathing tube 20 (step 1002), detecting the position of the person support apparatus 100 (step 1004), and the detection of the object and the position of the object (steps 1006 and 1008) are described in a specific order in the embodiment described and depicted in FIG. 10, it should be understood that these steps may be performed in any order or may be performed simultaneously. As described above, it is desirable that the breathing tube 20 is not impinged against the person support apparatus 100 during a surgical procedure to assist in ensuring that air or oxygen is provided to the subject without impediment. Accordingly, by providing an indication when the detected position of the breathing tube 20, the detected position of the person support apparatus 100, and the detected position of any objects 30 positioned within the field of view 80 of the first image capturing device 210 indicate that the breathing tube 20 is impinged against the person support apparatus 100, the surgical monitoring system 200 may assist medical staff in identifying when the breathing tube 20 is not positioned as desired.

Figure 11:
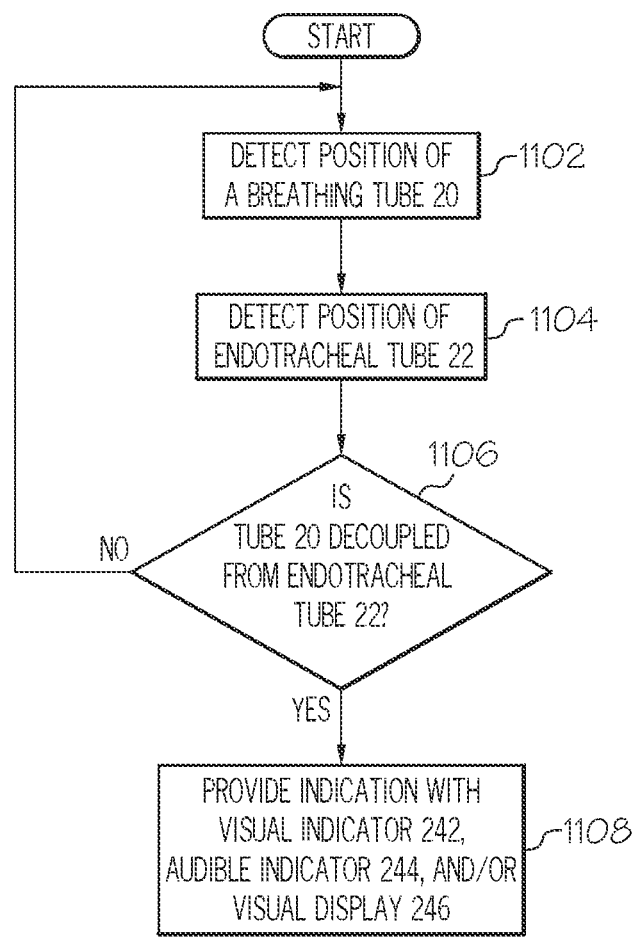
FIG. 11 schematically depicts another flowchart for one method of operating the surgical monitoring system of FIG. 1 according to one or more embodiments shown and described herein.

Referring to FIGS. 1, 4, 7A, 7B, and FIG. 11, another embodiment of a method of operating the surgical monitoring system 200 is depicted in the flowchart of FIG. 11. In a first step 1102, the machine vision sensor 220 detects a position of a breathing tube 20. In a second step 1104, the machine vision sensor 220 detects a position of an endotracheal tube 22. If the detected position of the breathing tube 20 and the endotracheal tube 22 indicate that the breathing tube 20 is decoupled from the endotracheal tube 22, the electronic controller 230 proceeds to step 1108, where the electronic controller 230 provides an indication with the visual indicator 242, the audible indicator 244, and/or the visual display 246. If the detected position of the breathing tube 20 and the endotracheal tube 22 indicate that the breathing tube 20 is not decoupled from the endotracheal tube 22, the electronic controller 230 proceeds back to step 1102, repeating the process.

While the steps of detecting the position of the breathing tube 20 (step 1102) and detecting the position of the endotracheal tube 22 (step 1104) are described in a specific order in the embodiment described and depicted in FIG. 11, it should be understood that these steps may be performed in any order or may be performed simultaneously. As described above, it is desirable that the breathing tube 20 is coupled to the endotracheal tube 22 to assist in ensuring that air or oxygen is provided to the subject without impediment. Accordingly, by providing an indication when the detected position of the breathing tube 20 and the detected position of the endotracheal tube 22 indicate that the breathing tube 20 is decoupled from the endotracheal tube 22, the surgical monitoring system 200 may assist medical staff in identifying when the breathing tube 20 is not positioned as desired.

While the embodiment described above with respect to FIGS. 7A, 7B, and 11 describe and depict the detection of the connection of a breathing tube 20 to an endotracheal tube 22, it should be understood the surgical monitoring system 200 may also provide an indication for other breathing tube arrangements, such embodiments in which the breathing tube 20 is connected to a mask (not depicted). In particular, the electronic controller 230 may provide an indication based on a detected position of the mask, providing an indication if the detected position of the mask indicates that the mask is not positioned on the face of a subject.

Figure 12:
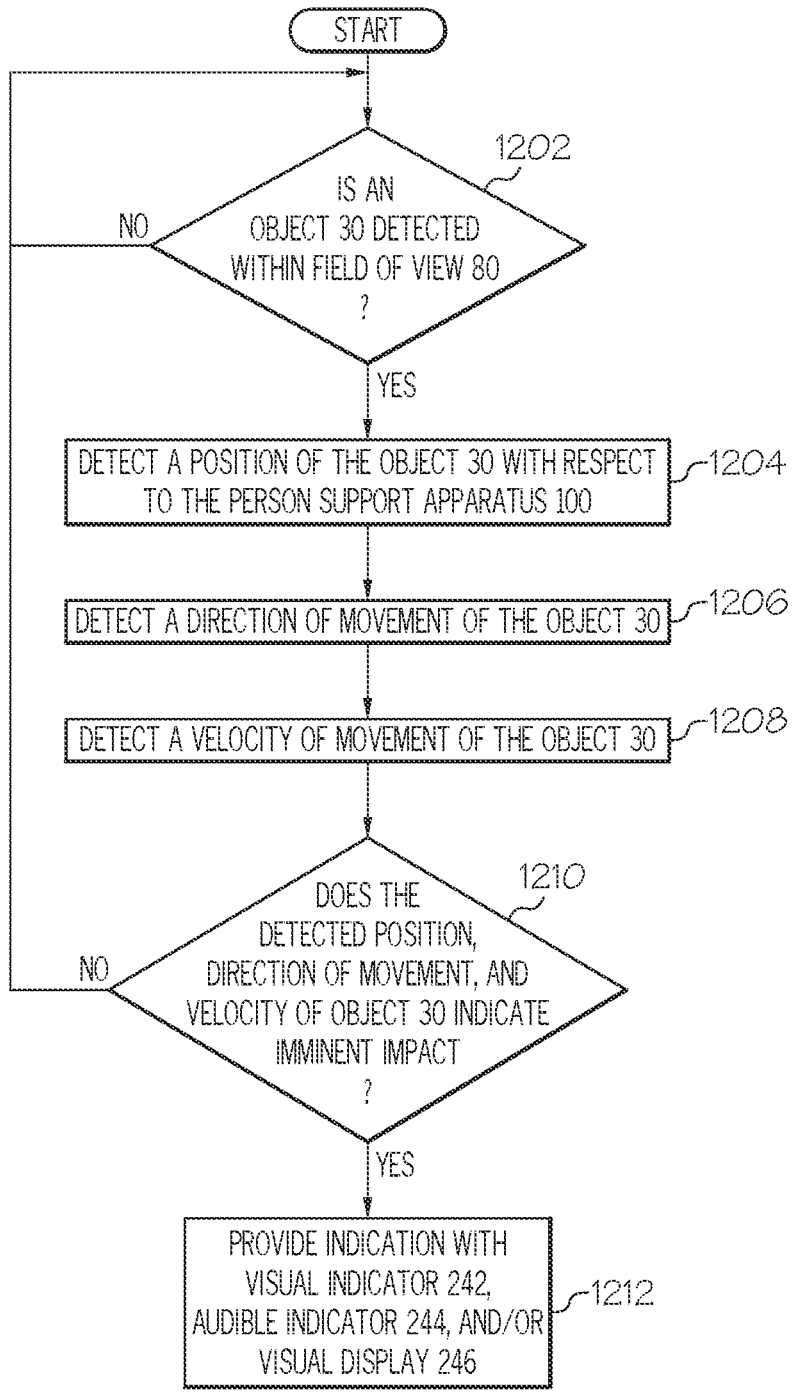
FIG. 12 schematically depicts another flowchart for one method of operating the surgical monitoring system of FIG. 1 according to one or more embodiments shown and described herein.

Referring to FIGS. 1, 4, 7, and 12, another embodiment of a method of operating the surgical monitoring system 200 is depicted in the flowchart of FIG. 12. In a first step 1202, the machine vision sensor 220 detects if an object 30 is positioned within a field of view 80 of the first image capturing device 210 and/or the field of view 82 of the second image capturing device 212 of the machine vision sensor 220. If an object 30 is not detected within the field of view 80, 82 of the machine vision sensor 220, the electronic controller 230 returns to step 1202. If an object 30 is detected within the field of view 80, 82 of the machine vision sensor 220, the electronic controller 230 proceeds to step 1204 and determines a position of the object 30 with respect to the person support apparatus 100 and/or lines 40 positioned around the perimeter 134 of the person support apparatus 100. The electronic controller 230 then proceeds to step 1206, and determines a direction of motion of the object 30 with respect to the person support apparatus 100. At step 1208, the electronic controller 230 detects a velocity of the object 30. At step 1210, the electronic controller 230 determines if the detected position of the object 30, the detected direction of movement of the object 30, and the detected velocity of the object 30 indicate an imminent impact with the person support apparatus 100 and/or the lines 40. If the electronic controller 230 determines that an impact is not imminent, the electronic controller 230 returns to step 1202. If the electronic controller 230 determines that an impact is imminent, the electronic controller 230 proceeds to step 1212, where the electronic controller 230 provides an indication with the visual indicator 242, the audible indicator 244, and/or the visual display 246.

While the steps of detecting the position of the object 30 (step 1204), detecting the direction of movement of the object 30 (step 1206), and the detection of the velocity of the object 30 (step 1208) are described in a specific order in the embodiment described and depicted in FIG. 12, it should be understood that these steps may be performed in any suitable order in which the velocity of the object 30 may be determined by comparing successive images of the object 30. In embodiments, "imminent impact" means that impact between the object 30 and the person support apparatus 100 and/or the lines 40 will occur within a predetermined amount of time based on the detected position, velocity, and direction of movement of the object 30. In embodiments, the predetermined amount of time is less than 5 seconds. In other embodiments, the predetermined amount of time is less than 3 seconds. In still other embodiments, the predetermined amount of time is less than 1 second.

As described above, while an object 30, such as a C-arm, may be moved adjacent to the person support apparatus 100 during a surgical procedure, it is undesirable for the object 30 to impact the person support apparatus 100 and/or the lines 40. Accordingly, by providing an indication when an imminent impact between an object 30 and the person support apparatus 100 is detected, the surgical monitoring system 200 may assist medical staff in identifying and avoiding potential impact between the object 30 and the person support apparatus 100 and/or the lines 40.

While methods of operating the surgical monitoring system 200 are described above including the detection of the position of a subject relative to the person support apparatus 100 (FIG. 9), the detection of impingement of a breathing tube 20 against the person support apparatus 100 (FIG. 10), the detection of the decoupling of a breathing tube 20 from an endotracheal tube 22 (FIG. 11, and the detection of an imminent impact with the person support apparatus 100 (FIG. 12), it should be understood that any of these methods may be performed alone or simultaneously by the surgical monitoring system 200.

It should now be understood that person support devices according to the present disclosure include a surgical monitoring system. The surgical monitoring system includes a machine vision sensor that may detect a position of a subject with respect to the person support apparatus, and provide a signal if the subject is not positioned as desired on the person support apparatus. Additionally or alternatively, the machine vision sensor may detect a position of a breathing tube with respect to the person support apparatus and may detect the position of objects proximate to the person support apparatus, providing a signal if the breathing tube is impinged against the person support apparatus by an object positioned proximate to the person support apparatus. In some embodiments, the vision system detects a position of an object proximate to the person support apparatus, detects a direction of movement and a velocity of the object, and provides a signal if the detected position, the direction of movement, and the velocity of the object indicate an imminent collision between the object and the person support apparatus. By providing an indication if the subject is positioned as desired on the person support apparatus, if a breathing tube is impinged against the support apparatus, and/or if an impact between an object and the person support apparatus is imminent, the surgical monitoring system may assist medical staff in identifying undesirable circumstances during a surgical procedure.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A surgical monitoring system comprising:
a machine vision sensor located under a person support apparatus configured to support a subject, wherein the machine vision sensor has a field of view including a breathing tube and an underside of an aperture of a head block of the person support apparatus;
an electronic controller communicatively coupled to the machine vision sensor, the electronic controller comprising a processor and a memory storing a computer readable instruction set, wherein, when the computer readable instruction set is executed by the processor, the electronic controller:
detects a position of the breathing tube;
detects a position of the person support apparatus;
detects a position of an object positioned within the field of view of the machine vision sensor;
compares the detected position of the breathing tube, the person support apparatus, and the object; and
determines if the detected position of the breathing tube, the person support apparatus, and the object indicates that the breathing tube is impinged between the object and the person support apparatus.

2. The surgical monitoring system of claim 1, wherein, when the computer readable instruction set is executed by the processor, the electronic controller further:
detects a position of the subject with the machine vision sensor;
detects the position of the person support apparatus;
compares the detected position of the subject with the detected position of the person support apparatus; and
determines if the detected position of the subject and the detected position of the person support apparatus indicates that the subject is not aligned with the person support apparatus.

3. The surgical monitoring system of claim 2, wherein the electronic controller is configured to detect a position of the aperture of the head block of the person support apparatus.

4. The surgical monitoring system of claim 3, wherein the electronic controller is configured to detect a position of eyes of the subject.

5. The surgical monitoring system of claim 4, wherein the electronic controller is configured to determine if the detected position of at least one of the eyes of the subject is not positioned within the aperture of the head block.

6. The surgical monitoring system of claim 2, wherein the electronic controller is configured to provide an indication if the detected position of the subject and the detected position of the person support apparatus indicate that the subject is not aligned with the person support apparatus.

7. The surgical monitoring system of claim 6, further comprising an audible indicator communicatively coupled to the electronic controller, wherein the electronic controller is configured to provide the indication with the audible indicator.

8. The surgical monitoring system of claim 1, further comprising a visual display communicatively coupled to the electronic controller, wherein the electronic controller is configured to send a signal to the visual display indicative of an image captured by the machine vision sensor.

* * * * *